United States Patent [19]
Baltimore et al.

[11] Patent Number: 5,358,856
[45] Date of Patent: Oct. 25, 1994

[54] GENE EXPRESSION IN MAMMALIAN CELLS USING A CAP INDEPENDENT 5' NONCODING REGION

[75] Inventors: David Baltimore, New York, N.Y.; Didier Trono, Solana Beach, Calif.

[73] Assignee: Whitehead Institute for Biomedical Research, Cambridge, Mass.

[21] Appl. No.: 887,223

[22] Filed: May 18, 1992

Related U.S. Application Data

[63] Continuation of Ser. No. 144,013, Jan. 14, 1988, abandoned.

[51] Int. Cl.⁵ ................ C12N 5/10; C12N 15/85; C12P 21/02
[52] U.S. Cl. ................ 435/69.1; 435/240.2; 435/320.1; 435/235.1
[58] Field of Search ............ 435/69.1, 172.3, 220, 435/240.2, 32, 34, 57, 60, 70; 536/27, 23.72

[56] References Cited

U.S. PATENT DOCUMENTS 4,937,190   6/1990   Palmenberg et al. .............. 435/69.1

OTHER PUBLICATIONS

Semler et al., *Nucleic Acids Res.* 12, 12 pp. 5123–15141, 1984.
Kitamura et al., *Nature*, vol. 291, 1981, pp. 547–553.
Trono, D. et al., *Science*, 241:445–448 (Jul. 22, 1988).
Shin, D. S. et al., *Journal of Virology*, 61:2033–2037 (Jun. 1987).
Krausslich, H. G. et al., *Journal of Virology*, 61:2711–2718 (Sep. 1987).
Shatkin, A. J. *Cell*, 40:223–224 (1985).
Etchison, D. et al., *Journal of Virology*, 51:832–837 (1984).
Sonenberg, N. *Advances in Virus Research*, 33:175–204 (1987).
Bernstein, H. D. et al., *Molecular and Cellular Biology*, 5:2913–2923 (1985).
Racaniello, V. R. and D. Baltimore, *Science*, 214:916–919 (1981).
Trono, D. et al., *Journal Virology*, 62:2291–2299 (1988).
Pelletier, J. et al., *Molecular and Cellular Biology*, 8:1103–1112 (1988).

*Primary Examiner*—Richard A. Schwartz
*Assistant Examiner*—James Ketter
*Attorney, Agent, or Firm*—Hamilton, Brook, Smith & Reynolds

[57] ABSTRACT

A construct which includes a cap independent 5' noncoding region of viral or cellular origin and a nucleotide sequence of interest, which is located downstream of the noncoding region. A method of producing a protein or a polypeptide of interest by introducing the construct, including a nucleotide sequence encoding the protein or the polypeptide of interest, into mammalian cells is also described. In one embodiment, the construct comprises all or a portion of the poliovirus cap independent 5' noncoding region and a nucleotide sequence encoding a protein or a polypeptide of interest.

11 Claims, 9 Drawing Sheets

FIG. 4A
FIG. 4B
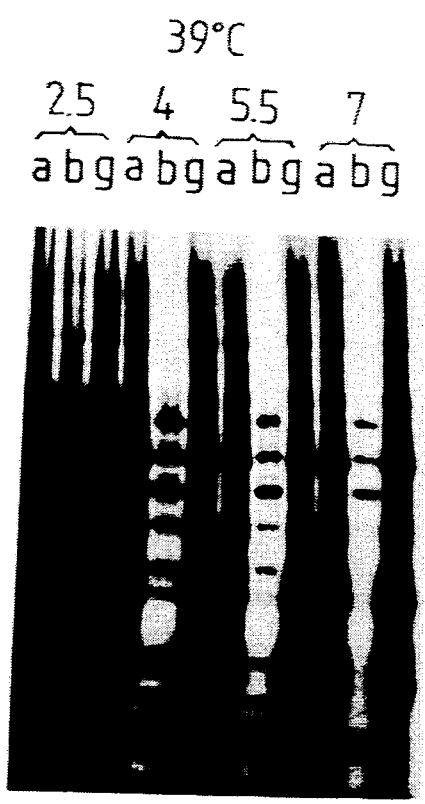
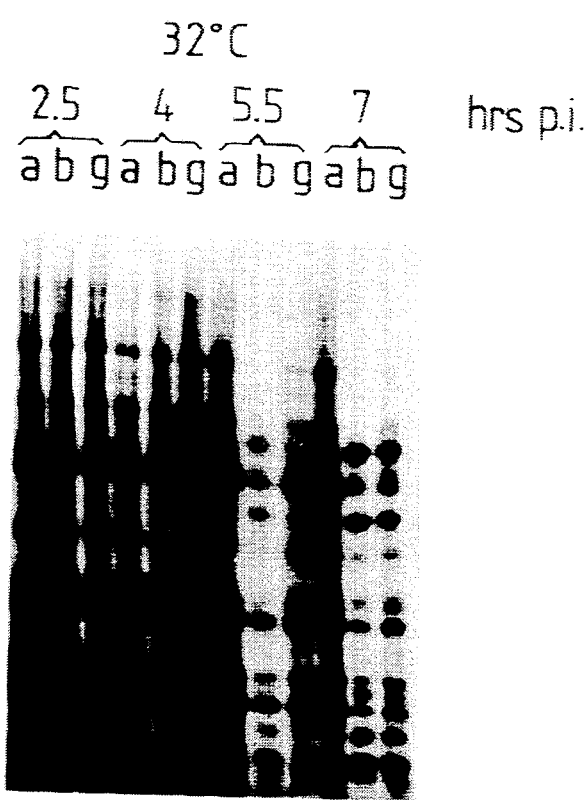

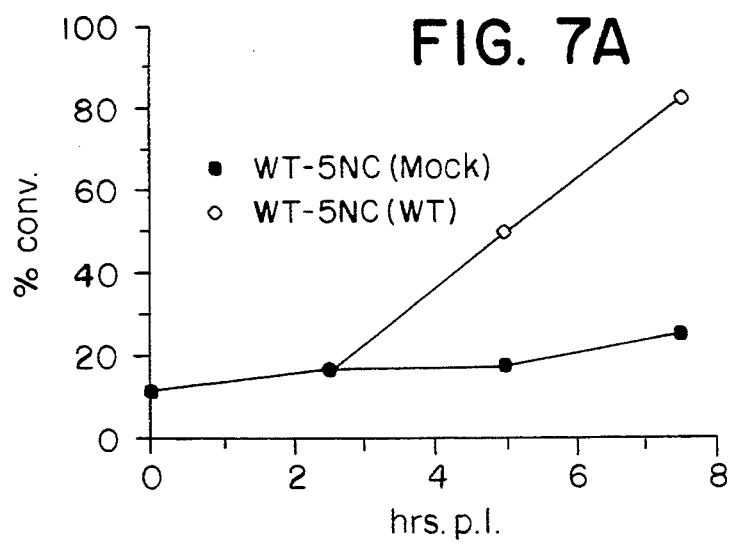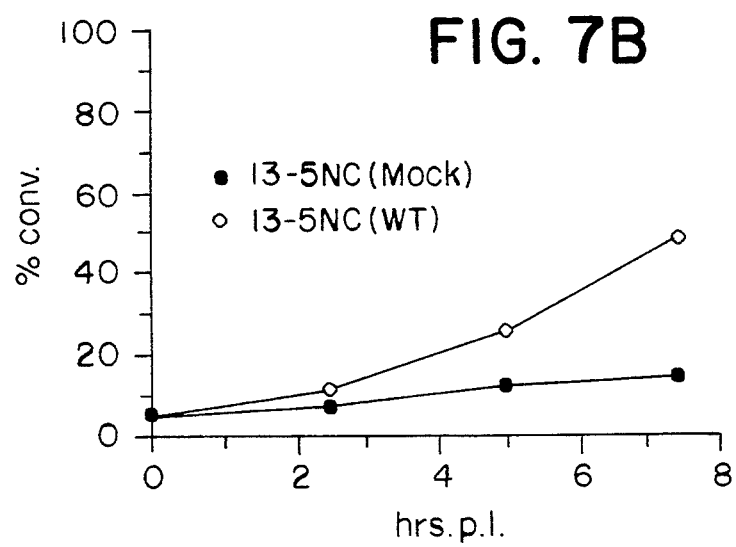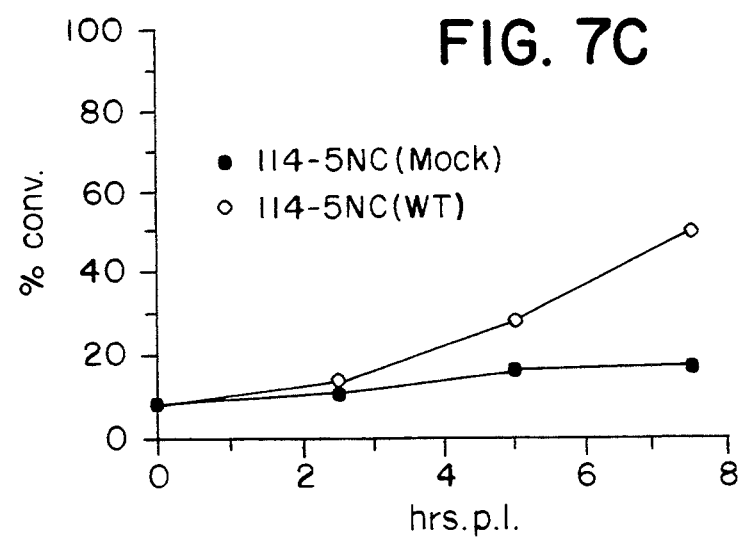

GENE EXPRESSION IN MAMMALIAN CELLS USING A CAP INDEPENDENT 5' NONCODING REGION

FUNDING

This is a continuation of application Ser. No. 07/144,013 filed on Jan. 14, 1988, now abandoned.

Work described herein was supported by a grant from the National Institutes of Health.

BACKGROUND OF THE INVENTION

The genome of poliovirus is a single-stranded molecule of messenger RNA polarity ("positive strand"), containing approximately 7500 nucleotides. Its 5' end is linked to a small peptide, VPg, and its 3' end is a stretch of poly(A) 40 to 100 nucleotides long. More than 800 noncoding nucleotides are located at the two ends of poliovirus RNA:742 at its 5' end and 65 preceding the poly(A) at its 3' end. An open reading fame initiated by an AUG at position 743 extends over 6528 nucleotides and encodes a polyprotein of about 250,000 daltons.

Unlike most eukaryotic mRNAs, picornaviral RNAs (e.g., poliovirus, encephalomyocarditis (EMC) virus) are not "capped" at their 5' end. Poliovirus terminates in pUp, instead of in the "capping" group $m^7G(5')ppp(5')N$ ... which is found on almost all other mRNAs. Recognition of the capped end of mRNA by one or more specific proteins has been shown to be important for gene expression. The cap structure appears to facilitate stable complex formation between 40S ribosomal subunits and mRNA during translation initiation. Sonenberg, N., *Advances in Virus Research*, 33:175–204 (1987). Poliovirus and other picornaviruses, however, translate their genomes in a cap-independent manner.

Infection of mammalian cells by a picornavirus is known to result in selective inhibition of host cell protein synthesis. In the case of poliovirus, selective inhibition occurs and translation of cellular mRNA steadily decreases as virus-specific translation increases. Within a short time (i.e., 2 to 3 hours) after infection, polioviral RNA is translated almost exclusively. Bernstein, H.D. et al, *Molecular and Cellular Biology*, 5:2913–2923 (1985).

The exact mechanism by which cap-dependent translation is inhibited in poliovirus-infected cells is still ill defined. However, it has been demonstrated that one of the poliovirus proteins, protein 2A, plays a critical role in this inhibition. One hypothesis as to the role of 2A is that, through the action of a cellular intermediate, it induces cleavage of eukaryotic initiation factor 4F, a component of the cap binding complex. The result is a decreased affinity of ribosomes for cellular mRNAs. It is thought that the poliovirus then takes advantage of the lack of competition by other mRNAs and translates its own genome with high efficiency.

SUMMARY OF THE INVENTION

The present invention is based on the determination that the 5' noncoding (NC) region of a genome which is translated in a cap-independent manner is responsible for translation in the cap-independent manner and that this ability is independent of the nature of the downstream open reading frame. In particular, it has been determined that the 5' noncoding region of the poliovirus genome is responsible for the ability of the virus to translate its genome in a cap-independent manner and that this ability is independent of the nature of the gene or nucleotide sequence located downstream of the noncoding region. That is, if a coding sequence other than the viral coding sequence is positioned downstream of the 5' NC region, it acquires the same property and is translated in a cap-independent manner.

Based on this discovery, a construct comprising a nucleotide sequence of interest and all or a portion of a viral or cellular cap independent 5' noncoding region and a system in which the nucleotide sequence of interest is expressed at enhanced levels have been developed, as has a method of producing the product (e.g., protein or polypeptide of interest) encoded by the nucleotide sequence of interest in a mammalian host.

The construct of the present invention comprises all or a portion of a 5' noncoding region of viral or cellular mRNA which is cap independent (i.e., the mRNA does not depend on a 5'-terminal cap for its translation) and a nucleotide sequence of interest, which is downstream of the 5' noncoding region. The construct is introduced into an appropriate mammalian host cell and the resulting construct-containing host cell is maintained under conditions appropriate for translation of the construct and production of the encoded protein or polypeptide.

In one embodiment, the construct is comprised of all or a portion of the 5' noncoding region of poliovirus and a nucleotide sequence encoding a protein or a polypeptide of interest. The construct is introduced into an appropriate mammalian host cell (e.g., any mammalian cell which has a poliovirus receptor). After sufficient time to allow mRNA from the nucleotide sequence of interest to be produced and to accumulate, cells are infected with poliovirus. Cap-dependent translation is quickly inhibited and, as a result, no new cellular protein is synthesized. In contrast, translation of cap-independent mRNAs (i.e., the poliovirus 5' noncoding region and nucleotide sequence of interest) is enhanced and the encoded protein or polypeptide is produced with a high degree of purity.

Using the method of the present invention, a nucleotide sequence or gene of interest can be expressed in a strictly selective manner in mammalian cells and, as a result, the encoded protein or polypeptide of interest, is produced with a high degree of purity.

The system and method of its use of the present invention can be used to express any gene of interest (produce the encoded protein or polypeptide) in mammalian host cells. It is particularly useful in producing a protein or polypepide which can be used as a drug or other pharmaceutical, or in producing single radiolabeled proteins or polypeptides in mammalian cells. The resulting protein or polypeptide can be removed or isolated by known techniques from the cells in which they are produced.

BRIEF DESCRIPTION OF THE DRAWINGS

FIG. 2A represents the growth curve of 5NC-13 (32.5° C.) FIG. 2B represents the growth curve of 5NC-13 (39.5° C. ) FIG. 2C represents the growth curve of 5NC-114 (37° C.).

FIG. 3A represents RNA synthesis for 5NC-11 (32.5° C. and 39.5° C. ). FIG. 3B represents RNA synthesis for 5NC-13(32.5° C. and 39.5° C. ). FIG. 3C represents RNA synthesis for 5NC-114 and 5NC-116 (37° C.) FIG. 3D represents progeny yield (as determined by plaque assay) and RNA synthesis comparison with wild type.

FIG. 4A. 4B 4C and 4D represents protein synthesis in virus-infected cells. FIG. 4A and 4B represents protein synthesis for 5NC-14 (39° C. and 32° C.). FIG. 4B represents protein synthesis for 5NC-114 and 5NC-116 (37° C.).

FIG. 7A, 7B and 7C are a graphic representation of expression of the gene encoding chloramphernical acetyltransferase (CAT) in cells super-infected with plasmids including the CAT gene and either the 5' noncoding region of wildtype poliovirus or a mutant of the 5' noncoding region of poliovirus.

DETAILED DESCRIPTION OF THE INVENTION

Figure 1:
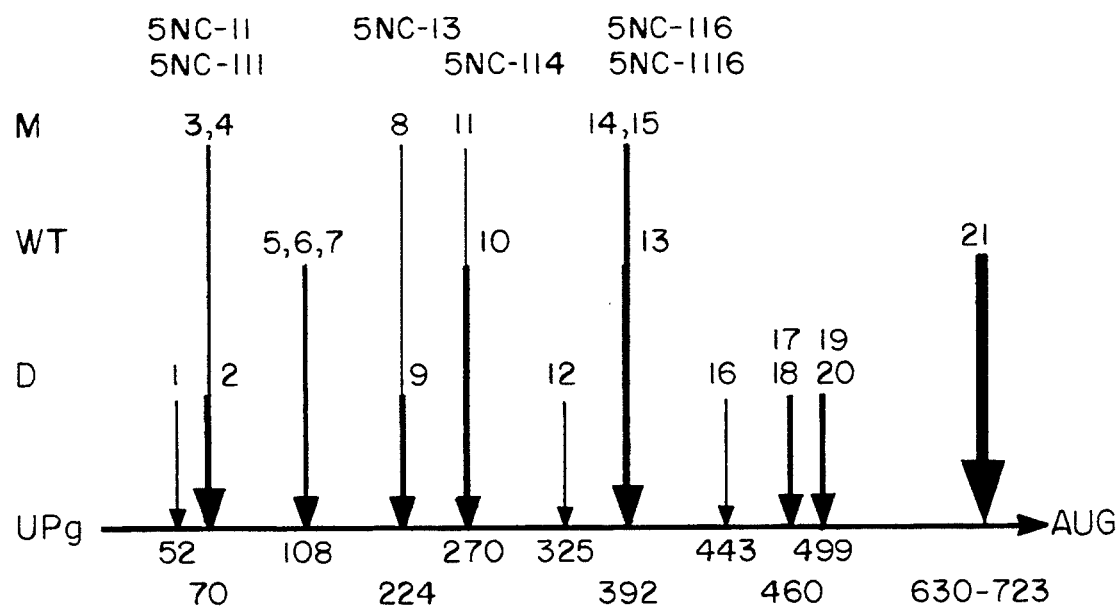
FIG. 1 presents results obtained from transfection of HeLa cells with RNA made from the 21 mutated clones described in Table 1. Numbers on top of each arrow correspond to the constructs described in Table 1 (i.e., 1 is pPN-1). Construct pPN-21 has a deletion of the sequence indicated on the bottom line. Short arrows indicate lethal mutations (D), medium length arrows denote silent mutations (WT), and long arrows point to mutations responsible for a recognizable viable phenotype (M). Names of the mutant viruses are shown at the top of the figure. Numbers on bottom lines indicate the nucleotide position of the mutation.

The present invention relates to a construct comprising RNA from the 5' noncoding (NC) region of viral or cellular RNA whose translation occurs in a cap-independent manner and a nucleotide sequence of interest, which is located downstream of the cap-independent 5' noncoding region; to a mammalian system for expression of the nucleotide sequence of interest; and to a method of their use, which results in production of the nucleotide of interest encoded product with a high degree of purity.

The construct of the invention comprises all or a portion of the 5' noncoding region of viral or cellular RNA which is translated in a cap-independent manner (referred to as a cap-independent 5' noncoding region) and a nucleotide sequence (referred to as a nucleotide sequence of interest) which encodes a product of interest.

The cap-independent noncoding region can be derived from viral RNA, such as picornavival RNA, or from cellular RNA. In one embodiment, the cap-independent 5' noncoding region of the polio virus is used. RNA can also be synthesized to have the same nucleotide sequence as all or a portion of the viral or the cellular cap-independent 5' noncoding region, or its functional equivalent. Synthesis can be carried out using recombinant DNA or RNA technology and cells can be engineered or modified to produce the desired nucleotide sequence. The desired nucleotide sequence can also be produced mechanically.

The nucleotide sequence of interest can be all or a portion of a gene of interest which encodes a protein or a polypeptide of interest, or a portion of the protein or the polypeptide of interest. The nucleotide sequence of interest is located downstream of the cap-independent 5' noncoding region. The two components of the construct are joined using art-recognized techniques and can be separated by only the nucleotides necessary for linking or joining them (e.g., linkers) or can be separated by an intervening coding or noncoding sequence.

The construct of the present invention can also include a promoter, which is located upstream of the cap-independent 5' noncoding region and allows for optimal transcription of the nucleotide sequence of interest. The construct can also include a polyadenylation site, located downstream of the nucleotide sequence of interest.

The construct of the present invention is introduced into an appropriate mammalian host cell, using art-recognized techniques. For example, the construct can be introduced into cells by transfection, electroporation or micro-injection. After introduction of the construct, cells are maintained under appropriate conditions for transcription of the nucleotide sequence in the construct and accumulation of the corresponding mRNA. Inhibition of cap-dependent translation is induced (e.g., by infecting the cell with poliovirus or by introducing a protein, such as poliovirus protein 2A, critical for inhibition of cap-dependent translation). As a result, cells containing the construct produce the encoded protein or polypeptide of interest, which is translated in a cap-independent manner. Cellular proteins are not synthesized and, thus, essentially "pure" or uncontaminated nucleotide sequence of interest-encoded protein or polypeptide is produced.

In the case in which a protein having a critical role in inhibition of cap-dependent translation is introduced into cells, the following method can be used: Two plasmids are introduced into an appropriate mammalian host cell by cotransfection. That is, one plasmid carrying a nucleotide sequence of interest downstream of a cap-independent 5' noncoding region, and a second plasmid carrying the genetic material encoding for 2A (or the portion required for its activity) are introduced into a mammalian cell. Protein 2A has been shown to be responsible for inhibition of cap-dependent translation in poliovirus-infected cells, apparently by inducing cleavage of eukaryotic initiation factor 4F, a component of the cap-binding complex.

Cells containing the two plasmids are maintained in culture, under conditions appropriate for translation of the two nucleotide sequences. As a result, cellular protein synthesis is inhibited, through the activity of protein 2A, and the nucleotide sequence of interest is expressed, resulting in the production of the encoded protein or polypeptide. In order to allow for accumulation of mRNA encoding the product of interest, the sequence encoding 2A can be placed under the control of an inducible promoter (for example the target of a transactivator, or a metallo-dependent promoter). The promoter controlling 2A expression is then induced only after significant transcription of the plasmid carrying the nucleotide sequence of interest.

It is also possible to construct cell lines which contain the cap-independent 5' noncoding region—gene of interest combination, a nucleotide sequence encoding protein 2A or portions thereof, an inducible promoter, a potential transactivator, or any combination thereof.

Cell lines constructed in this manner would constitutively express components incorporated into them.

Using the method of the present invention, a protein or polypeptide, such as an enzyme, hormone, growth factor or other drug, can be produced in enhanced quantities and essentially free of (uncontaminated by ) cellular proteins. Once produced, the protein or polypeptide can be removed or isolated from the host cell by using known techniques.

Demonstration that poliovirus 5' noncoding region contains elements essential for translation of the viral genome The following sections describe mutagenesis of the poliovirus 5' noncoding region, replication of viruses with mutations in the 5' region which result in a recognizable phenotype and genetic analysis of the 5' noncoding region mutants.

a. Mutagenesis of the poliovirus 5' noncoding region

Mutations in the 5' noncoding region of poliovirus type 1 (Mahoney) were created as follows: Multiple nucleotides were inserted or deleted at various sites, using a cDNA copy of poliovirus type 1 RNA. The procedures used are described below.

After the mutations were engineered into subclone pL1.4, they were introduced into the full-length clone pXpA, generating constructs pPN-1 to pPN-21. These constructs and their locations are described in Table 1 and FIG. 1. Using T7 RNA polymerase, RNA was made from all constructs, used to transfect HeLa cells, and the recovery of infectious virus particles was tested by plaque assay on HeLa cells. Three kinds of results were seen, as shown in Table 1 and FIG. 1.

of the 5' noncoding region were "lethal", meaning that no infectious virus particle was recovered from the transfected cells. Most of the 5' noncoding region appears, therefore, to be necessary for viral growth.

Second, five mutations at three different restriction sites (in pPN-5,-6,-7,-10,-13) did not affect the phenotype of the virus, at least as assessed by plaque assay. Another construct, pPN-21, with a deletion of bases 630 to 723, generated by the sequential use of Ball restriction enzyme and Ba131 exonuclease, also gave rise to virus with a wild type phenotype. Such a result has also been reported in Sabin 1 strain, where viruses lacking the genome region between nucleotides 600 and 725 are fully viable. Kuge, S. and A. Nomoto, *Journal of Virology*, 61:1478–1487 (1987). Thus, some regions can be altered without significantly inhibiting viral growth and one region is responsible for in vitro growth.

Third, six mutations affected four sites, all of which generated infectious viruses with a phenotype easily distinguishable from that of wild type. These mutations are as follows: Mutants 5NC-11 and 5NC-111:

Deleting bases 67 to 70 by eliminating the free overhang of a Kpn1 site was found to be "lethal: (pPN-2). However, duplicating the same four bases by filling in the overhang left by its isochizomer, Ban1 (pPN-3), generated mutant 5NC-11. The further addition of an EcoR1 linker at this filled in site (pPN-4) created mutant 5NC-111. Both mutants generate minute plaques compared to those of wild type virus, and are temperature sensitive (the titer at 32° C. is two-hundred fold more than the titer at 39° C.).

Mutant 5NC-13

The insertion of four bases at position 224, taking advantage of a BamH1 site (pPN-8), resulted in mutant 5NC-13. 5NC-13 is temperature sensitive (titer at 32° C. is one-hundred fold greater than titer at 39° C. ); moreover, the plaque it generates at both temperatures are smaller than those of wild type virus.

Mutant 5NC-114

TABLE 1

| | | MUTAGENESIS | |
|---|---|---|---|
| Clone | WT sequence | Mutant sequence | Phenotype* |
| pPN-1 | AGT$_{52}$ACT | AGT$_{52}$CCCGGGACT | D |
| pPN-2 | G$_{66}$GTACC | G$_{66}$....C | D |
| pPN-3 | GGTAC$_{70}$C | GGTAC$_{70}$GTACC | M (5NC-11) |
| pPN-4 | GGTAC$_{70}$C | GGTAC$_{70}$GGAATTCCGTACC | M (5NC-111) |
| pPN-5 | CTTA$_{108}$G | CTTA$_{108}$TTAG | WT |
| pPN-6 | CTTA$_{108}$G | CTTA$_{108}$GGAATTCCTTAG | WT |
| pPN-7 | CTTA$_{108}$G | CTTA$_{108}$GGAATTAATTCCTTAG | WT |
| pPN-8 | GGATC$_{224}$C | GGATC$_{224}$GATCC | M (5NC-13) |
| pPN-9 | GGATC$_{224}$C | GGATC$_{224}$GGAATTCCGATCC | D |
| pPN-10 | GAATC$_{270}$C | GAATC$_{270}$AATC | WT |
| pPN-11 | GAATC$_{270}$C | GAATC$_{270}$GGAATTCCAATC | M (5NC-114) |
| pPN-12 | GAGT$_{325}$C | GAGT$_{325}$AGTC | D |
| pPN-13 | CCATG$_{392}$G | CCATG$_{392}$CATGG | WT |
| pPN-14 | CCATG$_{392}$G | CCATG$_{392}$GAATTCCCATGG | M (5NC-116) |
| pPN-15 | CCATG$_{392}$G | CCATG$_{392}$GGAATTAATTCCCATGG | M (5NC-1116) |
| pPN-16 | GAAT$_{443}$C | GAAT$_{443}$GGAATTCCAATC | D |
| pPN-17 | GAATG$_{460}$CGGC | GAATG$_{460}$...GC | D |
| pPN-18 | GAATG$_{460}$CGGC | GAATG$_{460}$...GGAATTCC GC | D |
| pPN-19 | CAG$_{499}$TGATTG | CAG$_{499}$...TTG | D |
| pPN-20 | CAG$_{499}$TGATTG | CAG$_{499}$...GGAATTCCTTG | D |

*D: dead (lethal mutation)
WT: wild type (silent mutation)
M: mutant

First, nine mutations involving seven sites (those in pPN-1,-4,-9,-14,-16 to -20) distributed evenly over much The Hinf1 site at position 267 could be filled in without effect on the phenotype of the virus (pPN-10); the further insertion of an 8 bases linker (pPN-11) generated mutant 5NC-114. 5NC-114 is slightly temperature sensitive (five to ten-fold), and has a small plaque phenotype.

Mutants 5NC-116 and -1116

The insertion of four bases at position 392, by filling in a Nco1 site (pPN-13), did not significantly affect the size of viral plaques. When the same site was further modified by introduction of a linker (pPN-14) and when this linker was moreover blunted (pPN-15), mutants 5NC-116 and 5NC-1116, respectively, were obtained. Both mutants show a phenotype that resembles the one of 5NC-114 in temperature sensitivity and plaque size. The following procedures and materials were used in the mutagenesis described above.

DNA procedures

Restriction enzymes, T4 DNA polymerase and T4 DNA ligase were purchased from New England BioLabs, Inc., Beverley, Mass., DNA polymerase I (Klenow fragment) from Soehringer Mannheim Biochemicals, Indianapolis, Ind., exonuclease Bal 31 from Internation Biotechnologies Inc., New Haven, Conn., T7 RNA polymerase and human placenta RNase inhibitor from Promega Biotec, Madison, Wis., and avian myeloblastosis virus reverse transcriptase from Life Sciences Res., Baltimore, Md. All enzymes and compounds were used according to manufacturer's instructions.

Mutagenesis was done on a pBR-based subclone containing the first 1200 nucleotides of poliovirus type 1 (Mahoney) cDNA, downstream of a T7 RNA polymerase promoter (a modification of our original infectious clone). Racaniello, V. R. and D. Baltimore, *Science*, 214:916–919 (1981). The three protocols used were: filling in restriction sites (partial digestion with a restriction enzyme, blunting with Klenow, ligation); deleting restriction sites overhangs (partial digestion, blunting with T4 DNA polymerase, ligation); and inserting linkers at some restriction sites (partial digestion, blunting with Klenow or T4 DNA polymerase, linker ligation). The Aat2 site at position 1118 of poliovirus sequence was then used to introduce all the mutated 5' ends into the full-length clone. Plasmids were sequenced by the chemical technique. Maxam, A. M. and W. Gilbert., *Methods in Enzymology*, 65:499–560 (1980).

Cells and viruses:

HeLa and CV1 cells were grown as previously described. Bernstein, H. D. et al., *Molecular and Cellular Biology*, 5:2913–2923 (1985). HeLa cells on 100 mm dishes were transfected with 2 to 5 ug of in vitro synthesized RNA, using the DEAE-dextran procedure. Luthman, H. and G. Magnuson, *Nucleid Acids Research*, 11:1295–1308 (1983). All constructs were also tested by DNA transfection (average 10 ug) according to the same protocol. Generation of infectious virus particles was checked by covering the transfected cells with an agar overlay and examining the plates for plaques over 2 to 5 days, and also by harvesting cells that had been transfected, treating them by 3 cycles of freeze-and-thaw, and using them for a plaque assay on a new monolayer. Stocks from each viable virus were grown according to standard techniques. Bernstein, H. D. et al., *Molecular and Cellular Biology*, 5:2913–2923 (1985).

One-step growth curves

Measurement of virus growth and release was done on 60 mm-diameter HeLa cells dishes, according to standard procedures. Bernstein, H. D. et al., *Molecular and Cellular Biology*, 5:2913–2923 (1985).

Measurement of viral RNA synthesis

Monolayer cultures of HeLa cells were infected at a multiplicity of infection (MOI) of 10. After adsorption at room temperature for 30 minutes, Dulbecco modified Eagle medium (DME) supplemented with 7% fetal calf serum (Hazleton) was added. At various times after infection, cells were placed on ice, washed once with cold PBS, and lysed in 10 mM Tris-HCI pH 7.5, 10 mM NaCI, and 0.1% NP-40. Nuclei and debris were removed from centrifugation. RNA was isolated by phenol/chloroform extraction and ethanol precipitation. Portions were denatured in 10×SSC (1×: 0.15 M NaCl, 5 mM sodium citrate), 17% formaldehyde, and bound to nitrocellulose by aspiration with a dot-blot apparatus. Filters were baked for 2 hrs in 50% formamide, 5×SSCPE (1×: 1×SSC, 13 mM $KH_2PO_4$, 1 mM EDTA), 5×Denhardt's, 0.1% SDS, 250 ug/ml herring sperm DNA, 500 ug/ml yeast tRNA, and hybridized overnight at 60° C. in the same solution, using [$^{32}$P]RNA probes generated with SP6 or T7 polymerase as described. Melton, D. A., et al., *Nucleic Acids Research*, 12:7035–7056 (1984). The probes represented nucleotides 670–2243 of poliovirus type 1 Mahoney genome, in either direction. After hybridization, filters were washed in 0.2×SSC three times at 68° C. and exposed to X-ray film. Regions where RNA was bound were then cut out, dissolved in Biofluor (National Diagnostics), and radioactivity was measured with a scintillation counter.

Nucleotide sequencing of RNA

RNA from all viable viruses was prepared as above, and sequenced by the chain-termination technique using reverse transcriptase and synthetic oligonucleotides primers complementary to bases 120–143, 298–320, 477–500 or 758–781 of the viral RNA. Sanger, F. et al., *Proceedings of the National Academy of Sciences, USA*, 74:5463–5467 (1977).

Electrophoretic analysis of protein synthesis in infected cells

Infections were done as described above. At various times post-infection, cells were placed in methionine-depleted DME containing 25 uCi/ml of [$^{35}$S]methionine. After 30 minutes of incubation, cells were put on ice, washed once with cold PBS, harvested by centrifugation, and lysed in 10 mM Tris-HCI pH 7.5, 10 mM NaCI and 0.5% NP-40. Nuclei were removed by centrifugation, and a portion of the cytoplasmic extract was fractionated by electrophoresis through a 12.5% SDS-polyacrylamide gel. After electrophoresis, gels were treated with Autofluor (National Diagnostics), dried, and exposed to X-ray film at −70° C.

Immunoprecipitation of infected cell extracts

[$^{35}$S]methionine labeled cell extracts were immunoprecitated in IPB (20 mM Tris-HCI pH 7.5, 1% Triton X-100, 0.5% sodium deoxycholate, 0.1% SDS, 0.5 M NaCl, 1 mM EDTA), using a rabbit polyclonal poliovirus type 1 antivirion antiserum. After incubation for 1 hour on ice, the immune complexes were recovered by the addition of a 10% solution of *S. aureus*, washed three times with IPB, suspended in Laemmli sample buffer, boiled and centrifuged to remove the *S. aureus* cells. Laemmli, U. K., *Nature*, 291:547–553 (1970). The supernatants were analyzed by electrophoresis as described above.

Immunoblot analysis of p220

Cytoplasmic extracts were prepared as above, and an immunoblot analysis was performed as described by Bonneau and Sonenberg, using a rabbit anti-p220 polyclonal antiserum (a gift from I. Edery, McGill University, Montreal). Bonneau, A. M. and N. Sonenberg, *Journal of Virology*, 61:986–991 (1987).

Complementation experiments

HeLa or CV1 cell infections were performed at 39° C. in 60-mm diameter petri dishes, and yields of progeny virus measured at various times, as described by Bernstein et al. Bernstein, H. D. et al., *Journal of Virology*, 60:1040–1049 (1986). The complementation index (CI) was defined as follows: CI for mutant A=titer of mutant A in mixed infection/titer of mutant A in single infection, where titers are measured at the permissive temperature. Revertants and recombinants, identified by the size of plaques and/or by the loss of temperature sensitivity, were substracted from the counts.

b. Replication of viruses with mutations in the 5' region

Assuming that slightly different modifications of the same site would alter the same function, 5NC-111 and -1116 were not further characterized.

One-step growth curves

Figure 2A:
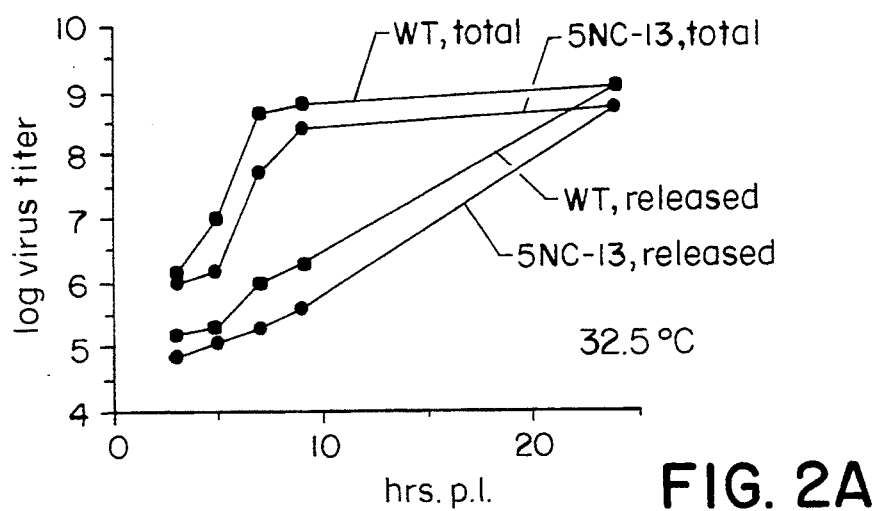
FIG. 2A, 2B and 2C represent the one-step growth curve of 5NC mutants. Infection was done on HeLa cell monolayers and virus released into the medium and total virus production were determined at each time point.
Figure 2B:
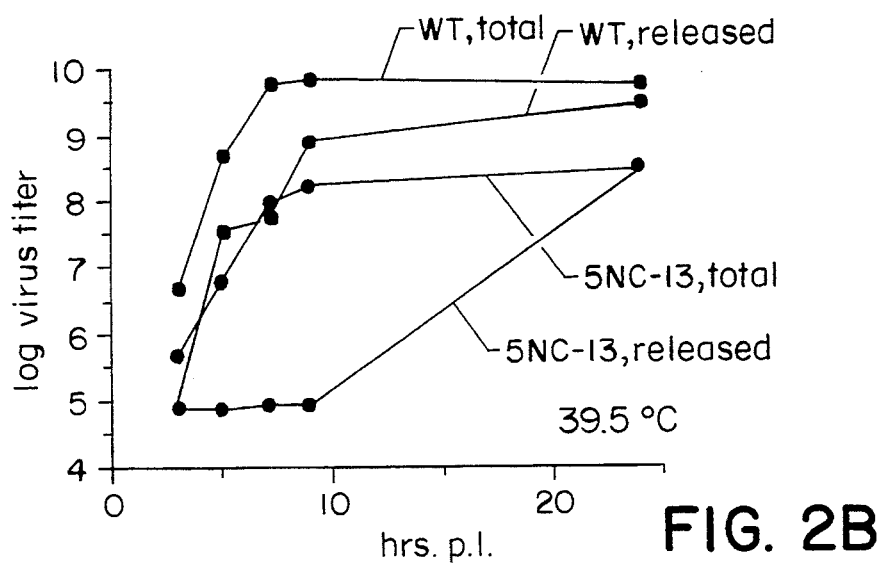
Figure 2C:
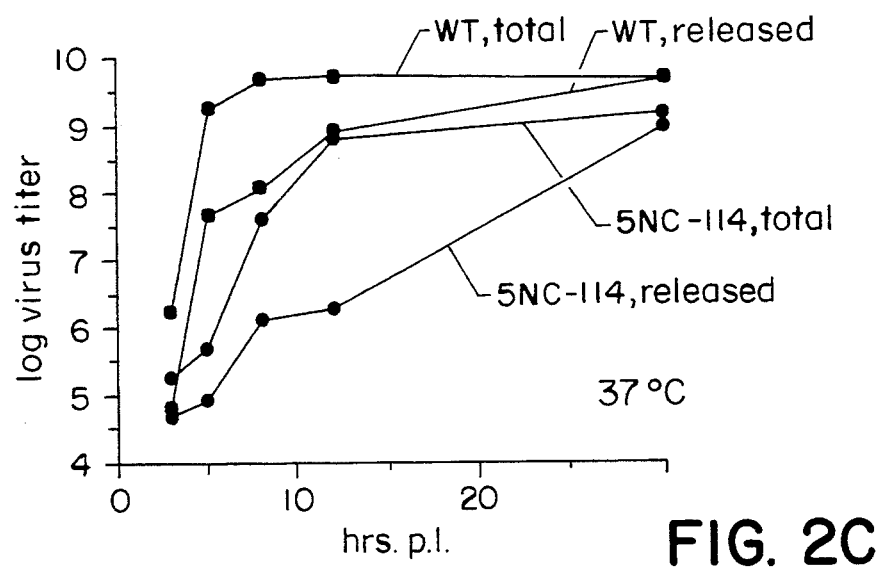

The defects in the four phenotypically mutant viruses were characterized by examination of some basic parameters of the poliovirus life cycle. One-step growth curves (FIGS. 2A, 2B and 2C) show that all of these mutants replicate more slowly than the wild type parental strain, and produce a final progeny yield that is lower.

Viral RNA synthesis

As a first step toward defining why their replication was inefficient, the ability of the 5' noncoding (5NC) mutants to synthesize RNA was assessed. This is usually done by measuring the incorporation of $^3$H-uridine into viral RNA in the presence of actinomycin D, a specific inhibitor of cellular transcription. However, replication of all of the 5NC mutants was sensitive to actinomycin D, in contrast to wild type virus. The reason for this sensitivity to actinomycin D is unknown, but has been reported in other mutants, mapping in the 5NC region or elsewhere. Racaniellio, V. R. and C. Meriam, *Virology*, 155:498–507 (1986). Therefore, viral RNA synthesis was analyzed by dot blot, as described above.

Figure 3A:
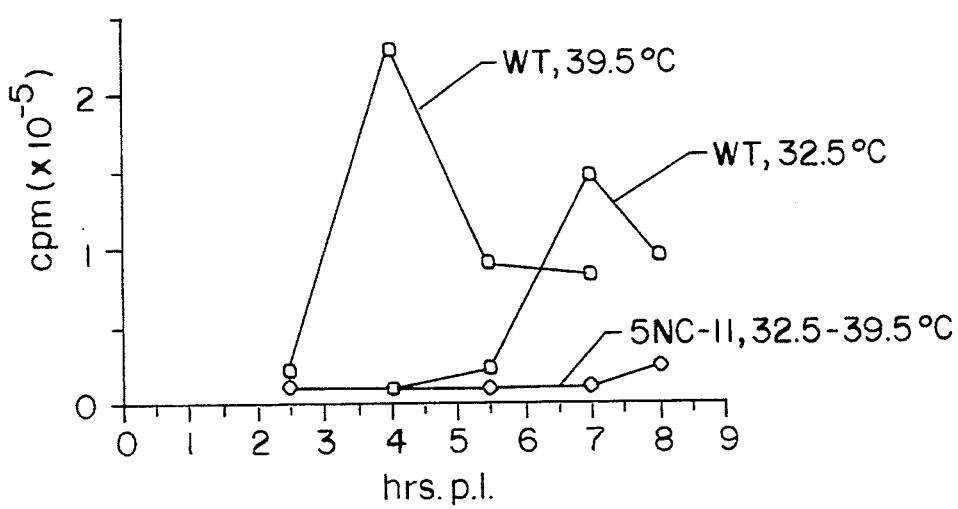
FIG. 3A, 3B, 3C and 3D represent RNA synthesis in virus-infected cells. The result of positive-strand is shown.

5NC-11 differed strikingly from 5NC-13, -114 and -116 with regard to viral RNA synthesis: at all temperatures 5NC-11 made less than 1% of the wild type amount of RNA (FIG. 3A).

Figure 3B:
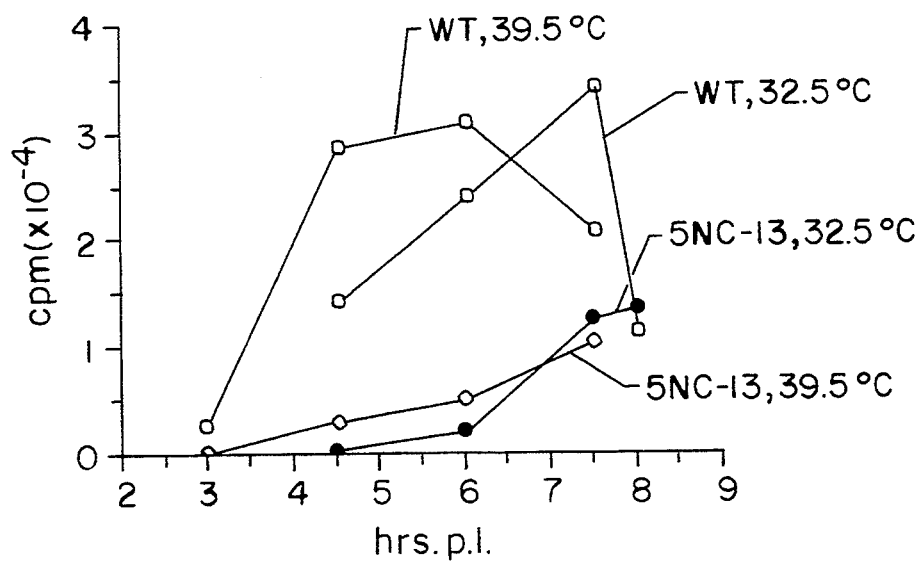
Figure 3C:
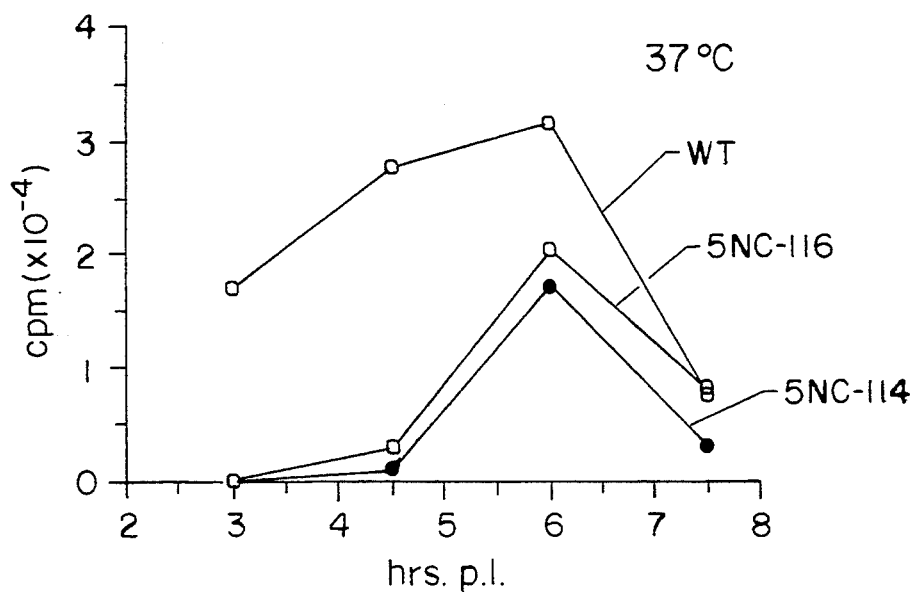

5NC-13, -114 and -116 all synthesized a significant amount of RNA. They made 30 to 60% of the wild type level of RNA, both plus and minus strand (FIGS. 3B and 3C). There was, however, a delay in RNA synthesis by all of the mutants. For instance, at 37° C., wild type RNA synthesis peaked at 4 hrs post-infection and 5NC-114 and -116 reached their maximal amount of RNA at 6 hrs post infection.

Figure 3D:
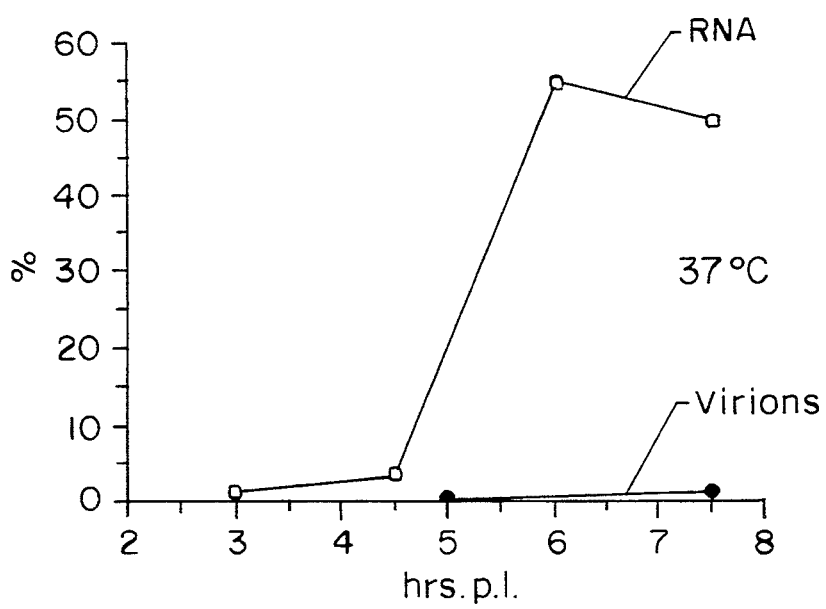

Although these three mutants are somewhat defective in RNA synthesis, this is not their primary defect. A comparison of progeny virion yield and RNA synthesis makes this point (FIG. 3D). For instance, at 6 hours post infection, 5NC-114 (and the others similarly) made, about 50% of the normal yield of RNA, with a normal ratio of single-to double-stranded RNA, but produced only 0.3% of the normal yield of progeny.

Protein synthesis in infected cells

Figure 4C:
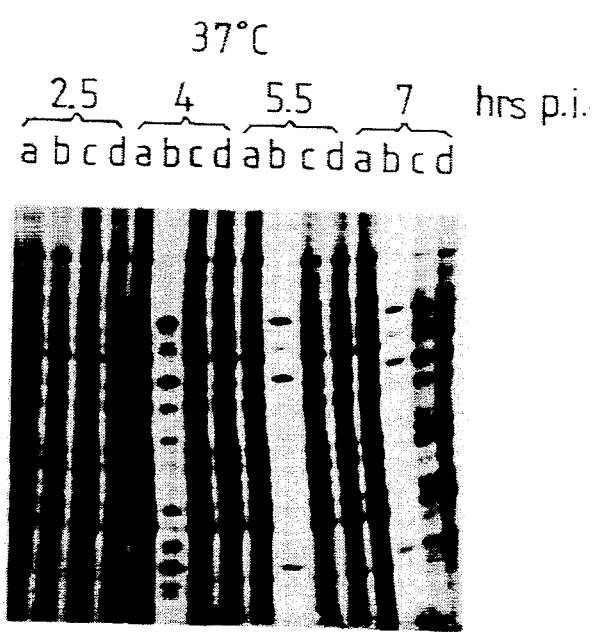
Figure 4D:
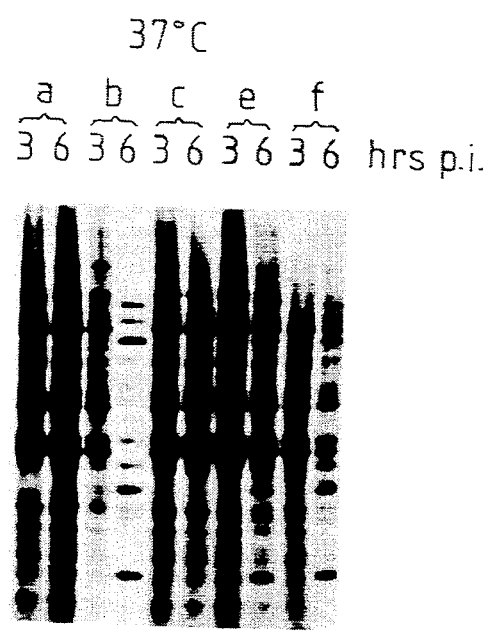
FIG. 4D represents the effect of increasing the initial multiplicity of infection (MOI) of 5NC-114. a: Mock-infected cells; b: wild type virus; c: 5NC-114; d: 5NC-116; e: 5NC-114(MOI:50 pfu/cell); f: 5NC-114 (MOI:100 pfu/cell); g: 5NC-13.
Figure 5:
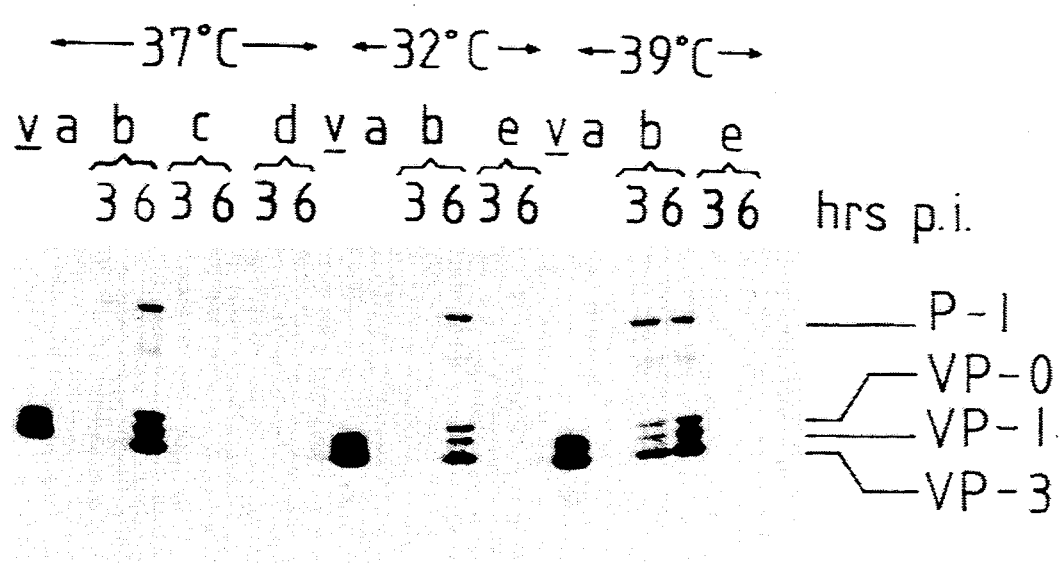
FIG. 5 presents analysis of viral-specific protein synthesis. v:$^{35}$S-methionine radiolabeled virion; a: mock-infected cells; b: wild type virus; c: 5NC-114; d: 5NC-116; e: 5NC-13.

The pattern of viral and cellular proteins synthesized in infected cells was analyzed in order to examine what might be the primary defect in these mutants. For this, cells were pulse-labeled with $^{35}$S-methionine at various times after infection, and cytoplasmic extracts were fractionated by electrophoresis through SDS-polyacrylamide gels. In striking contrast to wild type virus, 5NC-13, -114 and -116 did not shut off host cell translation, even late after infection (FIGS. 4A, 4B and 4C). This failure to induce shut off could be partly relieved by increasing the MOI, as shown with 5NC-114 (FIG. 4D) Virus-specific protein produced were resolved by immunoprecipitation of the extracts with antiviral antibodies that reacted with the capsid proteins (FIG. 5). In all three mutants, virus specific protein synthesis was markedly decreased compared to wild type. Detectable levels appeared only several hours after infection. The processing of the virion proteins appeared, however, to be normal: no excess of precursor accumulated at any point.

Fate of p220

Shut off of host cell translation correlates with the cleavage of one of the components of the cap-binding-complex, eukaryotic initiation factor 4F, also called p220. To examine whether the mutants failed to induce this cleavage, an immunoblot analysis of infected cell cytoplasmic extracts was carried out, using a polyclonal anti-p220 antibody. In wild type-infected cells, the cleavage of p220 was completed at 3 hr post-infection (at 37° C. or 39° C.). In mutant-infected cells, only partial cleavage was seen at 6 hrs post-infections; at its non-permissive condition (39°), 5NC-13 did not induce any cleavage of p220. As already seen with host cell translational shut off, a MOI effect was observed: when cells were infected with increasing MOIs of 5NC-114, a better, although still delayed, cleavage of p220 was observed.

c. Genetic analysis of the mutants

As demonstrated above, all three mutants examined here (5NC-13, 5NC-114, 5NC-116) behaved similarly in the infected cell. They showed poor viral protein synthesis, absence of host cell translational shut off, and significant, but delayed, viral RNA synthesis. The primary defect created by the mutations was not, however, clear. To define what the primary defect was, genetic analysis was carried out, by studying their ability to complement and be complemented by other well-defined polio mutants. In genetic complementation, cells are infected with one virus alone or with two viruses together. The yields of the single and mixed infections are compared. A complementation index is calculated from the ratio of these yields. If the growth of one of the partners is enhanced in mixed infection, it is then known to be defective in a function that can be provided in trans. The existence of defective interfering particles in poliovirus demonstrates that the capsid proteins can be provided in trans. It was also shown recently that two non-structural proteins, 2A and 3A, involved in translational shut off and RNA synthesis, respectively, carry out a trans rather than a cis activity; other nonstructural functions (2B, 3D, 3' noncoding region) seemingly act mainly in cis. Bernstein, H. D. et al., *Journal of Virology*, 60:1040–1049 (1986).

Figure 6:
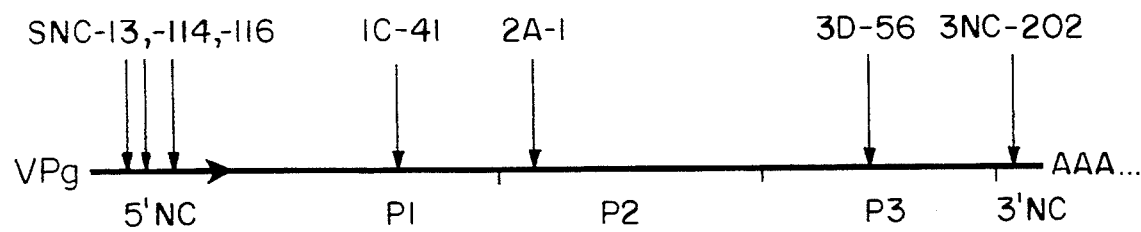
FIG. 6 is a schematic representation of mutants used in complementation experiments. The approximate genomic location of the mutants described herein is shown.

The complementation behaviour of the mutants was analysed by testing their ability to complement and be complemented by other well defined mutants. The following mutants were used: (FIG. 6) one mapping in the capsid region (1C-41): one in the replicase gene (3D-56): one in the 3' noncoding region (3NC-202): and two in the region encoding for the 2A protein. These latter two mutants, 2A-1 and R2-2A-2 (a gift from V. R. Racaniello), both exhibit an inability to induce host cell specific translational shut off, make a normal amount of RNA, and produce in HeLa cells an early global translational shut off, inhibiting both cellular and viral protein synthesis. Bernstein, H.D. et al., *Molecular and Cellular Biology*, 5:2913–2923 (1985). Cleavage of p220 is also not induced in HeLa cells infected with these mutants. To some extent, therefore, they produce phenocopies of 5NC-13, -114 and -116; a major difference is that the 5NC mutants do not induce a global shut off. The results of the complementation experiments are presented in Table 2.

TABLE 2

COMPLEMENTATION EXPERIMENTS[a]

| VIRUS PAIR | C.I.[b] AT 3 HRS. P.I. | C.I. AT 6 HRS. P.I. |
|---|---|---|
| 1) 5NC-13 + 5NC-114 | 1 (Total) | 1 (Total) |
|  | 1 (5NC-114) | 1 (5NC-114) |
|  | 15 (5NC-13) | 6 (5NC-13) |
| 2) 5NC-114 + 5NC-116 | 1.2 (total) | 1 (total) |
| 3) 5NC-13 + 5NC-116 | 1 (total) | 1.5 (total) |
| 4) 3NC-202 + 3D-56 | 1.3 | 1 |
| 5) 5NC-13 + 3NC-202 | 120 | 140 |
| 6) 5NC-114 + 3NC-202 | 150 | 43 |
| 7) 5NC-13 + 3D-56 | 180 | 50 |
| 8) 5NC-114 + 3D-56 | 40 | 20 |
| 9) 5NC-13 + 1C-41 | 90 | ND[c] |
| 10) 5NC-114 + 1C-41 | 40 | ND |
| 11) 3NC-202 + 2A-1[d] | 50 | ND |
| 12) 5NC-13 + 2A-1[d] | 1.2 (total) | ND |
|  | 20 (5NC-13) |  |
| 13) 5NC-114 + 2A-1[d] | 2 (total) | ND |
| 14) 3D-56 + R2-2A-2 | 40 | ND |
| 15) 5NC-13 + R2-2A-2 | 2 (total) | ND |
| 16) 5NC-114 + R2-2A-2 | 4 (total) | ND |

[a]the mutant complemented is underlined.
[b]complementation index (calculated as described previously)
[c]ND: not determined.
[d]done on CV1 cells.

The behavior of the 5NC mutants in complementation experiments is of particular interest because such mutants present a phenotype which is similar to mutants with lesions in the 2A protein (i.e., reduced level of protein synthesis and failure to inhibit host cell translation). The results of the complementation experiments are demonstrated by the following: First, 5NC-13, -114 and -116 did not complement each other (Table 2, lines 1 to 3). There was no enhancement of the total progeny yield in mixedly-infected cells, as compared to singly-infected cells. Thus, they fall in a single complementation group. When cells were infected at 39° C. with 5NC-13, a strongly temperature sensitive mutant, and 5NC-114, which does not exhibit the same degree of temperature sensitivity, the growth of 5NC-13 was enhanced, but only to a level that was still a few fold lower than the growth of 5NC-114. The growth of this latter mutant was itself not enhanced. This suggested that these mutants are defective to different degrees in the same function, and that this function can be provided in trans. The function made by the less defective mutant was available for use by both.

This analysis of one-way intragenic complementation was confirmed by the second type of result: the 5NC mutants were efficiently complemented by mutants 1C-41, 3D-56 and 3NC-202 (Table 2, lines 5 to 10), confirming the trans-acting nature of their defect. The three mutants that complemented the 5NC mutants grew very poorly, if at all, at 39° C., but they dramatically increased the progeny yield of the 5NC mutants in mixed infections. Therefore, they provided to the 5NC mutants a function that the 5NC mutants could not perform. As a control, 3NC-202 and 3D-56 did not detectably complement each other (line 4).

Third, mutants mapping in the 2A region did not efficiently complement and were not efficiently complemented by the 5NC mutants (Table 2, lines 12, 13, 15, 16), even though the 2A function is an easily complementable one (lines 11 and 14). Bernstein, H. D. et al., *Journal of Virology*, 60:1040–1049 (1986). It appears that mutations in the 5NC and the 2A region have deleterious consequences for the same function.

These results were confirmed by analysing $^{35}$S-methionine-labeled cytoplasmic extracts obtained from singly- and mixedly-infected cells. Compared to cells infected with a single virus, cells co-infected with 3NC-202 and one of the 5NC mutants showed an enhancement of host cell translational inhibition and of virus-specific protein synthesis. On the other hand, in HeLa cells co-infected with 2A-1 and one of the 5NC mutants, viral protein synthesis was not enhanced, specific shut off was not observed, and instead a global inhibition of translation, both viral and cellular, took place as in cells infected with 2A-1 alone. This last point makes a strong argument that the 5NC mutants are defective in providing the 2A function: if this were not the case, they should have been able to prevent a phenomenon thought to be a consequence of the absence of a functional 2A.

Exclusive expression in mammalian cells of a gene placed downstream of poliovirus 5' noncoding region The ability of the poliovirus 5' noncoding region to direct in mammalian cells the cap-independent translation of foreign sequences, and the influence of various mutations on that potential was assessed. Results demonstrate that poliovirus 5' noncoding region can direct cap-independent translation of foreign sequences. This was shown as follows: The gene encoding chloramphenicol acetyl transferase (CAT) was cloned at position 630 of poliovirus 5' noncoding region, either from the wild type sequence or from one of the mutated clones described earlier. In all cases, the constructs were placed under the control of the SV40 early promoter. These constructs, as well as a pSV2-CAT control, were introduced in parallel into Cos cells by electroporation. Forty hours later, a fraction of the cells that had been electroporated with each one of the constructs was harvested for CAT assay. At the same time, another fraction was infected with poliovirus at a MOI of 100, in the presence of guanidine (to inhibit poliovirus replication and therefore prevent early death of the cell) and actinomycin D (to stop any further accumulation of mRNA in all cases). A third fraction was Mock-treated, with addition of guanidine and actinomycin D to the medium. At various times later, an equal number of cells from each one of these two fractions was assayed for CAT activity.

Results are presented in Table 3 and demonstrated the following:

First, poliovirus infection of cells electroporated with a pSV2-CAT plasmid resulted in the abolition of further CAT synthesis (Table 3, line 1).

Second, CAT activity was stimulated by poliovirus infection in cells transfected with a construct in which wild type poliovirus 5' noncoding region preceded the CAT encoding sequence (Table 3, line 2). The same result was obtained when the leader sequence was the one of mutant 5NC-11, shown to contain a mutation without effect on the translation of the viral RNA but impairing its replication (Table 3, line 3).

Third, constructs corresponding to viable poliovirus mutants with a decreased translational potential (i.e., mutants 5NC-13, -114 and -116), showed a reduced baseline level of CAT activity, but had kept the ability to translate in a cap-independent manner. That is, they were stimulated by poliovirus infection (Table 3, lines 4, 6, 7).

Finally, constructs containing mutations that had been previously identified as "lethal" (see Table 1 and FIG. 1) were found to have lost the potential to translate in a cap-independent manner (Table 3, lines 5, 8 to 11).

This confirms the results described earlier, and also discloses what appear to be regions crucial to cap-independent translation. The sequence extending from nucleotides 460 to 500 seems critical in that regard.

This demonstrates that poliovirus 5' noncoding region can direct in mammalian cells the cap-independent translation of foreign sequences that are placed downstream. As a consequence, it provides a unique method to express genes of interest in mammalian cells with a high degree of purity.

TABLE 3

Expression of CAT Gene

|   | $t_o$ (40 hpe) | M7 | W7 | Phenotype of Clone |
| --- | --- | --- | --- | --- |
| 1. pSV$_1$·CAT | 6.5 | × 1.3 | × 0.8 | |
| 2. pXA·CAT = p5NC.CAT | 1.0 | × 1.4 | × 2.4 | WT |
| 3. pPN·3·CAT | 0.8 | × 1.4 | × 3.1 | M(5NC-11) |
| 4. pPN·8·CAT | 0.33 | × 2 | × 2.7 | M(5NC-13) |
| 5. pPN·9·CAT | 0.38 | × 1.9 | × 1.4 | D |
| 6. pPN·11·CAT | 0.73 | × 1.2 | × 2.0 | M(5NC-114) |
| 7. pPN·14·CAT | 0.75 | × 1.4 | × 2.2 | M(5NC-116) |
| 8. pPN·17·CAT | 0.56 | × 1.3 | × 0.7 | D |
| 9. pPN·18·CAT | 0.21 | × 1.2 | × 1.1 | D |
| 10. pPN·19·CAT | 0.29 | × 1.6 | × 0.9 | D |
| 11. pPN·20·CAT | 0.53 | × 1.3 | × 1 | D |

PN = proximal noncoding
$t_o$(40 hpe) = time zero (40 hours post electroporation)
WT = wild type (silent mutation)
M = mutant
D = dead (lethal mutation)

The Unitary Function of Region P: Role in Neurovirulence

The cumulative data from sets of experiments shows that an extensive RNA sequence is responsible for allowing translation of the viral RNA. It extends at least from nucleotides 220 to 500. Major and minor determinants of poliovirus RNA translation have been determined and minimal changes in some crucial regions (for instance a two or a three-base deletion at position 460 or 499, respectively) have been shown to completely abolish its ability to be translated in a cap-independent manner (thus explaining why no viable virus containing such mutations could be obtained). A likely possibility is that region P provides an internal ribosome binding site.

If the whole sequence contained within the limits of region P belongs to the same functional unit, it will include nucleotides that have been found to be major determinants of the attenuation of type 3 and, to a lesser extent, type 1 neurovirulence. This would suggest that attenuation in vaccine strains comes from a specific inability of motor neurons, as opposed to enterocytes, to translate the viral genome. It has been shown that vaccine strains translate more poorly than their wild type parents, at least in some in vitro systems. If such a model is true, defining how region P accomplishes its function may highlight some specific characteristics of the translational machinery in neurons. Also, the 5' noncoding region of poliovirus should be useful as target to engineer new vaccines which have full immunogenic properties and better stability than currently used vaccines.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method of producing a protein or a polypeptide of interest in mammalian cells, wherein the protein or the polypeptide is not a poliovirus protein or polypeptide, comprising the steps of:
    a) introducing into mammalian cells a construct comprising the following components:
        1) the poliovirus cap independent 5' noncoding region and
        2) a nucleotide sequence encoding a protein or a polypeptide of interest which is not a poliovirus protein or polypeptide and is positioned downstream of the poliovirus cap independent 5' noncoding region, thereby producing cells containing the construct;
    b) maintaining cells containing the construct under conditions appropriate for production of the corresponding mRNA;
    c) inducing inhibition of cap dependent translation, thereby inhibiting cellular protein synthesis in cells containing the construct; and
    d) maintaining cells containing the construct under conditions appropriate for cap independent translation to occur, whereby the protein or polypeptide which is not a poliovirus protein or polypeptide is produced in a cap-independent manner.

2. A method of claim 1 wherein the poliovirus cap independent 5' noncoding region contains a mutation a site from base 70 to base 442 and a and inhibition of cap dependent translation is induced by infecting cells containing the construct with poliovirus or by introducing a gene encoding poliovirus protein 2A into cells containing the construct.

3. A method of producing a protein or a polypeptide of interest in mammalian cells, wherein the protein or the polypeptide is not a poliovirus protein or polypeptide, comprising the steps of:
    a) introducing into mammalian cells a construct comprises the poliovirus cap independent 5' non-coding region containing a mutation at a site selected from the group consisting of: base 70, base 224, base 270 and base 392; a nucleotide sequence encoding the protein or the polypeptide of interest which is not a poliovirus protein or polypeptide; and the SV40 early promoter wherein the poliovirus cap independent 5′ noncoding region and the nucleotide sequence encoding the protein or the polypeptide which is not a poliovirus protein or polypeptide are under the control of the SV40 early promoter;

b) maintaining cells containing the construct under conditions appropriate for accumulation of corresponding mRNA;

c) inducing inhibition of cap dependent translation by introducing into cells produced in (b) a nucleotide sequence encoding poliovirus protein 2A or the portion thereof which inhibits cap-dependent translation, thereby inhibiting production of cellular proteins; and d) maintaining cells produced in (c) under conditions appropriate for cap independent translation to occur, whereby the protein or the polypeptide which is not a poliovirus protein or polypeptide is produced in a cap independent manner.

4. A method of producing a protein or a polypeptide of interest in mammalian cells, wherein the protein or the polypeptide is not a poliovirus protein or polypeptide, comprising the steps of:

a) co-transfecting mammalian cells with:

1) a first construct comprising the poliovirus cap independent 5′ noncoding region containing a mutation selected from the group consisting of insertion after 70 of base GTAC; insertion after base 70 of bases GGAATTCCGTAC; insertion after base 224 of bases GATC; insertion after base 270 of bases GGAATTCCAAT; insertion after base 392 of bases GGAATTCCCATG; and insertion after base 392 of bases GGAATTAATTCCCATG; a nucleotide sequence encoding the protein or the polypeptide of interest which is not a poliovirus protein or polypeptide, the nucleotide sequence encoding the protein or polypeptide which is not a poliovirus protein or polypeptide positioned downstream of the 5′ noncoding region; and the SV40 early promoter, wherein the poliovirus cap independent 5′ noncoding region and the nucleotide sequence encoding the protein or polypeptide which is not a poliovirus protein or polypeptide are under the control of the SV40 early promoter and 2) a second construct comprising an inducible promoter and a nucleotide sequence encoding poliovirus protein 2A or the active portion thereof, under the control of the promoter;

b) maintaining cells containing the two constructs under conditions appropriate for production of mRNA encoding the protein or polypeptide of interest and inactivity of the inducible promoter;

c) inducing the inducible promoter, thereby producing poliovirus protein 2A or the active portion thereof and inhibiting cellular protein synthesis; and d) maintaining cells produced in (c) under conditions appropriate for cap independent translation to occur, whereby the protein or polypeptide of interest is produced in a cap-independent manner.

5. A mammalian cell line capable of constitutive expression of the poliovirus cap independent 5′ noncoding region, the cell line having incorporated therein the poliovirus cap independent 5′ noncoding region and a nucleotide sequence of interest which encodes a protein or polypeptide which is not a poliovirus protein or polypeptide and is located downstream of the poliovirus cap independent 5′ noncoding region such that expression of said protein or polypeptide is driven by the poliovirus cap independent 5′ noncoding region.

6. A mammalian cell line of claim 5 further comprising an inducible promoter and a nucleotide sequence encoding poliovirus protein 2A under the control of the inducible promoter.

7. A construct for producing a protein or a polypeptide encode by a nucleotide sequence of interest, the construct comprising the poliovirus cap independence 5′ noncoding region and the nucleotide sequence of interest, in which the nucleotide sequence of interest is position downstream of the poliovirus 5′ noncoding region and is a nonpoliovirus nucleotide sequence operably linked to the poliovirus cap independent 5′ noncoding region such that expression of the nonpoliovirus nucleotide sequence is driven by the poliovirus cap independent 5′ noncoding region.

8. A construct of claim 7 wherein the poliovirus cap independent 5′ noncoding region contains a mutation at a site from base 70 to base 442.

9. A construct of claim 8 wherein the mutation in the poliovirus cap independent 5′ noncoding region is at a site selected from the group consisting of base 70, base 224, base 270 and base 392.

10. A construct for producing a protein or a polypeptide encoded by a nucleotide sequence of interest, comprising:

a) the poliovirus cap independent 5′ noncoding region including nucleotides 460 to 500;

b) the nucleotide sequence of interest; and c) the SV40 early promoter, wherein the nucleotide sequence of interest is located downstream of the poliovirus 5′ noncoding region is a nonpoliovirus nucleotide sequence operably linked to the poliovirus cap independent 5′ noncoding region such that expression of the nonpoliovirus nucleotide sequence is driven by the poliovirus cap independent 5′ noncoding region, and the poliovirus cap independent 5′ noncoding region and the nonpoliovirus sequence of interest are under the control of the SV40 early promote.

11. A construct of claim 9 wherein the mutation in the poliovirus cap independent 5′ noncoding region is selected from the group consisting of: insertion after base 70 of bases GTAC; insertion after base 70 of bases GGAATTCCGTAC; insertion after base 224 of bases GATC; insertion after base 270 of bases GGAATTCCAAT; insertion after base 392 of bases GGAATTCCCATG; and insertion after base 392 of bases GGAATTAATTCCCATG.

* * * * *